(12) United States Patent
Rheinberger et al.

(10) Patent No.: US 6,180,688 B1
(45) Date of Patent: Jan. 30, 2001

(54) ION-RELEASING COMPOSITE MATERIAL

(75) Inventors: Volker Rheinberger, Vaduz (LI); Ulrich Salz, Lindau (DE); André Rumphorst, Vaduz (LI); Kurt Grabher, Feldkirch (AT); Urs Karl Fischer, Arbon (CH); Norbert Moszner, Eschen (LI)

(73) Assignee: Ivoclar AG (LI)

( * ) Notice: Under 35 U.S.C. 154(b), the term of this patent shall be extended for 0 days.

(21) Appl. No.: 09/210,510

(22) Filed: Dec. 11, 1998

Related U.S. Application Data
(60) Provisional application No. 60/094,019, filed on Jul. 24, 1998.

(30) Foreign Application Priority Data

Dec. 15, 1997 (DE) ................................................ 197 57 647

(51) Int. Cl.[7] ................................................ A61K 6/083
(52) U.S. Cl. ........................................................ 523/116
(58) Field of Search ............................................... 523/116

(56) References Cited

U.S. PATENT DOCUMENTS

| 4,224,023 | | 9/1980 | Cheung . | |
|---|---|---|---|---|
| 4,388,069 | | 6/1983 | Orlowski . | |
| 5,306,338 | * | 4/1994 | Tsunekawa | 523/116 |
| 5,658,963 | * | 8/1997 | Qian et al. | 523/116 |

FOREIGN PATENT DOCUMENTS

| 44 45 266 A1 | 6/1996 | (DE) . |
|---|---|---|
| 0 382 033 A2 | 8/1990 | (EP) . |
| 0 449 399 A2 | 10/1991 | (EP) . |

* cited by examiner

*Primary Examiner*—Peter F. Kulkosky
(74) *Attorney, Agent, or Firm*—Nixon Peabody LLP

(57) ABSTRACT

The invention relates to ion-releasing composite materials on the basis of polymerizable monomers. The material is characterized in that it contains one or more non-acid, non-ionic, hydrophilic crosslinker monomers, one or more non-acid, non-ionic, hydrophilic dilution monomers having a viscosity of ≦1 Pas and at least one ion-releasing filler. The materials are suitable in particular for use as dental materials.

16 Claims, No Drawings

ION-RELEASING COMPOSITE MATERIAL

This application claims priority benefit of U.S. patent application Ser. No. 60/094,019, filed on Jul. 24, 1998, which is hereby incorporated by reference.

The invention relates to composite materials on the basis of one or more non-acid, non-ionic, hydrophilic crosslinker monomers and one or more non-acid, non-ionic, hydrophilic dilution monomers having a viscosity of <1 Pas, which are suitable in particular as dental materials.

Dental materials which are capable of releasing ions, such as for example fluoride, calcium or hydroxide ions, in the oral cavity are increasingly of interest because of their remineralizing, bioactive and cariostatic action.

Restorative dental materials which display a caries-inhibiting action because they contain sources of fluoride, such as special chlorohexidine-fluoride compounds, are known e.g. from U. Salz, Phillip Journal 14 (1997) 296.

Further examples of ion-releasing dental materials are glass ionomer cements and compomers whose organic matrix is made up at least in part from acid monomers, oligomers or polymers (A. D. Wilson, J. W. McLean, Glasionomer Cement, Quintessence Publishers, Chicago 1988; J. Nicholson, M. Anstice, Trends Polym. Sci. 2 (1994) 272; R. Hickel, L. Kremers, C. Haffner, Quintessenz 47 (1996) 1581).

Glass ionomer cements are water-containing, two-component cements on the basis of polymeric organic acids such as for example poly(acrylic acid) and powdery, solid bases such as calcium-fluoride-aluminium silicate glasses. The curing of the cement takes place through ionic reaction between polymer-bound COOH groups and the calcium or aluminium ions emerging from the filler, so that the components of the glass ionomer cement can be mixed only shortly before use. This is laborious, and moreover the inclusion of air is unavoidable in most cases, which adversely affects the strength of the material. Because of their poor bending strength, glass ionomer cements are not suitable for occlusion-bearing fillings.

The term compomers is taken to mean compositions which are composed of polymerizable acid monomers and ion-releasing glass particles. They are anhydrous single-component systems which cure through radical polymerization of the monomer matrix. Acid-base reaction takes place to a small extent only when water is absorbed into the filling via saliva. The non-cured materials are moisture-sensitive, and uncontrolled contact with water, for example during production or storage, leads to a premature curing which makes the material unusable. Compomers have a greater mechanical strength than glass ionomer cements, but frequently display a smaller ion release.

Both glass ionomer cements and compomers generally display a high ion-release capacity when the matrix of the materials has an adequate hydrophilic character which encourages absorption of water. In the case of glass ionomer cements, the matrix is formed by polyalkene acids, whereas in the case of compomers it is above all carboxylic acid-containing monomers that are used as matrix materials. However, since a high water content or a high water absorption has a disadvantageous effect on the mechanical properties of polymers, it was not previously possible to produce materials having a high ion-release capacity which simultaneously display a high mechanical strength.

EP 0 449 399 B1 discloses as underfilling materials suitable composites on the basis of ion-releasing fillers and a mixture of customary dental monomers, such as e.g. the di-methacrylate of ethoxylated bisphenol-A, a hydrophobic dimethacrylate, with the urethane dimethacrylate comprising 2-hydroxyethyl methacrylate and 2,2,4-trimethyl hexamethylene diisocyanate, which do not contain acid monomers but do display only a small ion release.

The object of the invention is to provide composite materials having a high ion-release capacity and high mechanical strength capacity which are storage-stable in the uncured state even under moist conditions and whose mechanical properties are not substantially impaired after curing by the addition of water.

This object is achieved by composite materials on the basis of polymerizable monomers which are characterized in that the material contains a mixture of (a) at least one non-acid, non-ionic, hydrophilic crosslinker monomer, (b) at least one non-acid, non-ionic, hydrophilic dilution monomer having a viscosity of <1 Pas and (c) at least one ion-releasing filler.

The term crosslinker monomers is taken to mean monomers which contain at least two, preferably 2 to 4 groups capable of polymerization per monomer molecule.

The monomers are hydrophilic, i.e. they are capable of hydrophilic interactions with the filler. Monomers are preferred which contain one or more, preferably 1 to 2 urethane and/or OH groups, preferably OH groups. It was also found that these groups promote ion transport or ion emission.

The term non-acid compounds is taken to mean monomers which carry no strongly acidic groups such as carboxyl, phosphoric acid, phosphonic acid, phosphinic acid or sulphonic acid groups and which preferably also contain no weakly acid groups such as phenolic OH groups or SH groups or CH-acid groups such as β-diketone or β-diketoester groups.

Non-ionic monomers within the meaning of this invention are those which contain no ionic groups such as cationic ammonium or sulphonium groups or anionic acid residue groups of the strongly acid groups named above.

Preferred crosslinker monomers are 2,2-bis-4-(3-methacryloxy-2-hydroxypropyl)-phenylpropane) (bis-GMA), i.e. the reaction product of glycidyl methacrylate and bisphenol-A (containing OH groups), and 7,7,9-trimethyl-4,13-dioxo-3,14-dioxa-5,12-diaza-hexadecan-1,16-diyl-dimethacrylate (UDMA), i.e. the urethane dimethacrylate comprising 2 moles of 2-hydroxyethyl methacrylate (HEMA) and 1 mole of 2,2,4-trimethyl hexa-methylene diisocyanate (containing urethane groups). Also preferred as crosslinker monomers are reaction products of glycidyl methacrylate with other bisphenols, such as e.g. bisphenol-B (2,2'-bis-(4-hydroxyphenyl)-butane), bisphenol-F (2,2'-methylene diphenyl) or 4,4'-dihydroxydiphenyl), as well as reaction products of 2 mol HEMA or 2-hydroxypropyl (meth)-acrylate preferably with 1 mole of known diisocyanates, such as e.g. hexamethylene diisocyanate, m-xylylene diisocyanate or toluylene diisocyanate.

The term dilution monomers is taken to mean monomers having a viscosity of <1 Pas, preferably <100 mpas, which are suitable for diluting the generally highly viscous crosslinker monomers and thus permit the production of composites with a high filler content. The viscosity data relate to a temperature of 23° C. The viscosity is measured by means of a plate or rotation viscometer in accordance with DIN 53018.

The dilution monomers likewise contain at least two, preferably two to three groups capable of polymerization and at least one, preferably 1 to 2 OH and/or urethane groups, preferably OH groups. They are non-ionic and non-acid compounds.

A particularly preferred dilution monomer is glycerol dimethacrylate (GDMA). Other preferred dilution monomers can be produced by reaction of low-viscosity di- or triepoxides, such as for example ethylene glycol diglycidyl ethers, glycerol triglycidyl ethers or trimethylolpropane triglycidyl ethers with (meth)acrylic acid. Further preferred are also the reaction products of 2 or 3 moles of methacrylic acid with glycerol triglycidyl ether or trimethylolpropane triglycidyl ether. The term "low-viscosity" is taken to mean substances having a viscosity of <200 mPas, preferably <100 mPas (23° C.).

Preferred groups capable of polymerization are, in the case of both crosslinker monomers and dilution monomers, methacryl and/or acryl groups, in particular methacryl groups.

To produce composite materials, crosslinker monomers and dilution monomers are mixed with fillers, initiators for radical polymerization and optionally other auxiliaries. Single-component composite materials, i.e. composite materials which contain all the necessary components, are preferred.

The composite materials according to the invention preferably have the following composition:

(a) 1 to 40 wt.-%, particularly preferably 10 to 30 wt.-% and quite particularly preferably 15 to 25 wt.-% crosslinker monomer;

(b) 2 to 40 wt.-%, particularly preferably 2 to 30 wt.-% and quite particularly preferably 5 to 20 wt.-% dilution monomer;

(c) 30.0 to 94.0 wt.-% filler;

(d) 0.01 to 5 wt.-%, particularly preferably 0.1 to 2.0 wt.-% of an initiator for radical polymerization as well as optionally other additives.

The filler content depends crucially on the intended use of the composite material and is preferably 30 to 60 wt.-%, particularly preferably 40 to 60 wt.-%, in the case of securing cements, and 60 to 94 wt.-%, preferably 70 to 85 wt.-%, in the case of filling composites.

The composite materials preferably contain at least 5 wt.-%, particularly preferably at least 10 wt.-% of hydroxyl group-containing monomers, i.e. monomers having at least one hydroxyl group per monomer molecule.

The uncured materials can contain up to 1.0 wt.-% water without the stability in storage of the materials or the mechanical properties of the cured materials being impaired. This considerably facilitates both the production and the processing of the materials by the dentist or dental technician.

The materials according to the invention preferably contain as a maximum 2 wt.-% of monofunctional monomers, i.e. monomers having only one unsaturated group capable of polymerization, such as for example 2-hydroxyethyl(meth) acrylate.

The known initiators for cold, hot and photocuring are suitable as initiators for radical polymerization. Suitable initiators are described for example in the Encyclopedia of Polymer Science and Engineering, Vol. 13, Wiley-Intersci. Pub., New York etc. 1988, pp. 754 et seq.

Preferred initiators are azo-compounds, such as azobis (isobutyronitrile) (AIBN) or azobis(4-cyanovaleric acid) or peroxides, such as dibenzoyl peroxide, dilauroyl peroxide, tert.-butyl peroctoate, tert.-butyl perbenzoate ordi-(tert.-butyl)-peroxide.

Benzpinacol and 2,2'-di($C_1$–$C_8$-alkyl)benzpinacols are particularly suitable as initiators for hot curing.

Suitable photoinitiators for the UV or visible range are described by J. P. Fouassier, J. F. Rabek (Pub.), Radiation Curing in Polymer Science and Technology, Vol. II, Elsevier Applied Science, London and New York 1993, pages 155 to 237. Preferred photoinitiators are benzoin ethers, dialkyl benzil ketals, dialkoxyacetophenones, acylphosphonic oxides, α-diketones, such as 10-phenanthrenequinone, diacetyl, furil, anisil, 4,4'-dichlorobenzil and 4,4'-dialkoxybenzil and camphor quinone.

Dibenzoyl peroxide, camphor quinone and acylphosphinic oxides are preferred for the production of dental materials.

Suitable as fillers are all the ion-releasing fillers known for the production of glass ionomer cements. Fillers releasing $Ca^{2+}$, $F^-$ and/or $OH^-$ ions, such as are described in the publications named above or in DE 39 41 629 and in U.S. Pat. No. 4,814,362, are preferred.

Particularly preferred fillers are glass powders of fluoroaluminium silicate glasses with an average particle size of 0.05 to 15 μm, preferably 0.5 to 5.0 μm, which contain as principal constituents silicon oxide, aluminium oxide and calcium oxide (cf. A. D. Wilson, J. W. McLean, Glasionomerzement, Quintessence Verlags GmbH, Berlin 1988, pages 21 et seq.).

Preferred glasses are obtained by melting 25 to 45 wt.-% $SiO_2$, 15 to 40 wt.-% $Al_2O_3$, 0 to 10 wt.-% $AlF_3$, 0 to 30 wt.-% CaO, 0 to 10 wt.-% $Na_2O$, 0 to 15 wt.-% $CaF_2$, 0 to 15 wt.-% NaF and 0 to 25 wt.-% $AlPO_4$.

A particularly preferred glass has the following composition: 25 wt.-% $SiO_2$, 16.2 wt.-% $Al_2O_3$, 8.8 wt.-% $AlF_3$, 12.8 wt.-% NaF, 13 wt.-% $CaF_2$ and 24.2 wt.-% $AlPO_4$.

Dental materials which release calcium hydroxide or fluoride have proved themselves in dentistry. Through the controlled emission of calcium hydroxide and fluoride, the formation of secondary dentin is promoted and an alkalizing action vis-à-vis the pulpa is achieved, which protects the latter against acids and bacterial attacks.

Fillers which release alkaline ions are not compatible with acid monomers, however, and bring about a spontaneous curing of the matrix. Single-component composites which release calcium hydroxide are therefore either not stable or display only a small ion release when non-acid monomers are used.

The monomers used according to the invention contain no acid groups and can therefore be combined with alkaline fillers without problems. They allow the production for the first time of single-component composites which release calcium hydroxide and have a high ion-release capacity.

The term alkaline fillers is taken to mean fillers with alkaline components such as CaO, $Ca(OH)_2$ or $Na_2O$ which display an alkaline reaction in combination with water.

Preferred alkaline fillers are calcium hydroxide, calcium oxide and in particular calcium hydroxide-releasing glasses, i.e. glasses with a high calcium oxide content.

Glasses with a CaO content of at least 20 wt.-%, preferably 40 to 75 wt.-% and in particular 45 to 60 wt. % are preferred.

A preferred glass powder with a high calcium oxide content is described in EP 0 449 399 B1 and contains 40 to 75 wt.-%, preferably 45 to 60 wt.-% calcium oxide, 5 to 30 wt.-%, preferably 15 to 28 wt.-% boron oxide and 5 to 35 wt.-%, preferably 10 to 30 wt.-% silicon dioxide. The average particle size (weight average) of the glass powder lies between 1 and 100 μm, preferably 10 and 30 μm.

Further preferred are transparent glasses with a high calcium and fluoride ion emission, which contain the following components:

| Component | wt.-% |
|---|---|
| $SiO_2$ | 24.0 to 56.0 |
| CaO | 26.0 to 57.0 |
| F | 4.0 to 14.0. |

The transparent glasses used according to the invention preferably contain in addition at least one of the following components

| Component | wt.-% |
|---|---|
| $Na_2O$ | 1.0 to 9.0 |
| $B_2O_3$ | 1.0 to 14.0 |
| MgO | 1.0 to 14.0 |
| SrO | 1.0 to 12.0 |
| ZnO | 1.0 to 7.0 |
| $Al_2O_3$ | 0.5 to 5.0 |
| $ZrO_2$ | 0.5 to 4.0. |

Preferred quantity ranges exist for the individual components of the transparent glasses. These can be chosen independently of one another and are as follows

| Component | wt.-% |
|---|---|
| $SiO_2$ | 30.0 to 54.0 |
| | in particular 36.0 to 54.0 |
| CaO | 32.0 to 50.0 |
| F | 5.0 to 12.0 |
| $Na_2O$ | 1.0 to 8.0 |
| $B_2O_3$ | 1.0 to 12.0 |
| MgO | 1.0 to 10.0 |
| SrO | 1.0 to 10.0 |
| ZnO | 1.0 to 5.0 |
| $Al_2O_3$ | 0.5 to 4.0 |
| $ZrO_2$ | 0.5 to 4.0. |

Particularly preferred quantity ranges of the components of the transparent glass, which can be chosen independently of one another, are as follows

| Component | wt.-% |
|---|---|
| $SiO_2$ | 45.0 to 54.0 |
| CaO | 35.0 to 50.0 |
| F | 6.0 to 12.0 |
| $Na_2O$ | 4.0 to 7.0 |
| $B_2O_3$ | 1.0 to 12.0 |
| MgO | 1.0 to 10.0 |
| SrO | 1.0 to 10.0 |
| ZnO | 1.0 to 5.0 |
| $Al_2O_3$ | 0.5 to 4.0 |
| $ZrO_2$ | 0.5 to 4.0. |

All the quantities that are given above and in the following in the description and in the claims of the components of the transparent fluoride-containing glasses are to be understood as values which were obtained as follows. The quantities of the oxides were ascertained by quantitative determination of the corresponding cations, i.e. Si, Ca, Na, B, Mg, Sr, Zn and Al, by means of X-ray fluorescence analysis and conversion of the obtained values into the quantities of corresponding oxides. Thus the level of a cation serves as a basis for deducing the level of the corresponding oxides. In contrast to this, the quantity of $F^-$ is determined directly by means of an electrode which is selective for fluoride ions after the glass had been subjected to a soda-potash dissolution.

As a result of the high F-contents of the transparent glasses, there is formation to a noticeable extent of fluorides, such as e.g. $CaF_2$, in the glass. Therefore, the calculated oxide contents and accordingly the absolute oxygen content of the glass are too high, and the sum of the components exceeds 100%. The portion going beyond 100% is therefore shown as so-called "fluorine-equivalent oxygen". This is customary for silicate glasses containing fluoride and is described at length e.g. in J. Lange "Rohstoffe der Glasindustrie", Deutscher Verlag für Grundstoffindustrie, Leipzig, Stuttgart (1993), pp. 221–223.

It is generally customary in glass manufacture to add small quantities of fluoride as flux in order to improve the melting behaviour of the glass in question. However, the overall structure of the glasses is not substantially changed by these small portions of fluoride.

In contrast to this, a high fluoride portion of at least 4,0 wt.-% incorporated into the transparent glass used according to the invention, which substantially changes the basic structure of the glass compared with corresponding glasses which are free from fluoride or have only small fluoride contents as a result of the use of flux. A marked degradation of the $SiO_4$ tetrahedron network structure of the glass occurs because of this high fluorine content and the simultaneous incorporation of other network transformer ions, such as e.g. $Ca^{2+}$ or $Na^+$. A glass structure forms which can no longer be explained by the classical network theory. The glass structure comes close to a new glass structure which is called "inverted glass structure". The term inverted glass is taken to mean a glass which has less than 50 mol.-% network-former material.

As a result of the changed structure, it is above all the refractive index of the glass which changes, and surprisingly an emission of fluorine ions with a simultaneous emission of calcium ions from the glass is also possible. When the composite material is used in the dental field, the desired alkaline action can therefore be brought about in the oral cavity by the calcium ions together with carbonate in the saliva, and, through the fluoride ions, their known remineralizing action. Calcium ions also promote the remineralization process.

Furthermore, the high fluoride content of the glass brings about a marked reduction in its refractive index to values below 1.60 and preferably below 1.56. The organic matrix of the composite forming through curing of the polymerizable monomer has a very similar refractive index, for which reason the whole composite material can likewise be translucent or even transparent. This is naturally of particular advantage if the composite material is to be used for the production of visible dental restorations, which naturally are to have similar optical properties to translucent natural dental material.

To produce the transparent glass used according to the invention, suitable raw materials, in particular oxides, carbonates and fluorides, are mixed and melted at temperatures of in particular 1000 to 1600° C. to form a glass. The glass melt that forms is then quenched by being poured into water. The obtained transparent glass frit is then ground, dried and can be combined with polymerizable monomer to give the polymerizable composite material according to the invention.

The glass is customarily used as powder, the average size of the particles customarily being 1 to 100 μm and preferably 10 to 30 μm relative to the number of particles.

The ion-releasing fillers named above can be combined with other fillers, the proportion of ion-releasing fillers being at least 5 wt.-%, preferably 15 to 70 wt.-%.

Particularly suitable as further filler components are amorphous, spherical materials on the basis of mixed oxides from $SiO_2$, $ZrO_2$ and/or $TiO_2$ having an average particle size of 0.005 to 2.0 μm, preferably of 0.1 to 1 μm, such as are disclosed for example in DE-PS 32 47 800, microfine fillers, such as pyrogenic silica or precipitation silica as well as macro- or mini-fillers, such as quartz, glass ceramic or glass powder having an average particle size of 0.01 to 20 μm, preferably 0.5 to 5 μm, as well as X-ray-opaque fillers, such as ytterbium fluoride. The term mini-fillers is taken to mean fillers having a particle size of 0.5 to 1.5 μm and the term macro-fillers to describe fillers having a particle size of 10 to 20 μm.

In addition, the compositions according to the invention can, in case of need, contain further auxiliaries, in particular stabilizers, UV absorbers, dyestuffs, pigments and/or slip agents. The term stabilizers is taken to mean those substances which prevent a premature polymerization and thus above all increase the stability in storage of monomer mixtures and composites, without however impairing the properties of the cured materials. Preferred stabilizers are hydroquinone mono-methyl ether (MEHQ) and 2,6-di-tert.-butyl-4-methylphenol (BHT).

It was surprisingly found that, through the simultaneous use of the crosslinker and dilution monomers named above, compositions having a high ion-release capacity can be obtained which are storage-stable in the uncured state even in moist conditions and whose mechanical properties are not significantly worsened by the addition of water. The monomer mixtures according to the invention can be processed without problems with alkaline fillers to produce single-component composites.

The invention is described further in the following with reference to embodiments.

EXAMPLES 1 TO 5

As starting materials for the production of hydrophilic composites, monomer mixtures having the compositions given in Table 1 were produced and then processed to give the single-component composite pastes shown in Table 2.

TABLE 1

Composition of the monomer mixtures

| Monomer | Mixture (in mass-%) | | | | |
|---|---|---|---|---|---|
| | 1 | 2*) | 3 | 4*) | 5*) |
| bis-GMA[1] | 39.0 | 42.0 | 42.0 | 42.0 | 42.0 |
| UDMA[2] | 30.0 | 37.1 | 27.8 | 27.8 | 27.8 |
| GDMA[3] | 30.0 | — | 29.4 | — | — |
| TEGDMA[4] | — | 20.0 | — | 29.4 | — |
| HEMA[5] | — | — | — | — | 29.4 |
| Initiator/additives[6] | 1.0 | 0.8 | 0.8 | 0.8 | 0.8 |

*)Comparative example
[1]Bisphenol-A-glycidyl methacrylate (Esschem)
[2]7,7,9-trimethyl-4,13-dioxo-3,14-dioxa-5,12-diazahexadecan-1,16-diyl-dimethacrylate (Ivoclar)
[3]Glycerol dimethacrylate (Röhm)
[4]Triethylene glycol dimethacrylate (Esschem)
[5]2-hydroxyethyl methacrylate (Röhm)
[6]Initiator: camphor quinone; accelerator: N-(2-cyanoethyl)-N-methylaniline; inhibitor: hydroquinone monomethyl ether

TABLE 2

Composition of the composite pastes

| Monomer | Mixture (in mass-%) | | | | |
|---|---|---|---|---|---|
| | 1 | 2*) | 3 | 4*) | 5*) |
| Monomer mixture[1] | 22.0 | 22.1 | 22.3 | 22.3 | 22.3 |
| Alkali glass, sil.[2] | 48.0 | 52.2 | — | — | — |
| SP-2034, sil.[3] | 11.0 | — | 60.1 | 60.1 | 60.1 |
| YbF$_3$[4] | 12.0 | 10.0 | 11.6 | 11.6 | 11.6 |
| Aerosil-OX-50 ®, silanized[5] | 4.0 | 3.8 | — | — | — |
| Sphärosil ® sil.[6] | — | — | 6.0 | 6.0 | 6.0 |
| HDK-2000[7] | 3.0 | 2.4 | — | — | — |
| Ba-glass sil. (GM 27884)[8] | — | 9.5 | — | — | — |

[1]The monomer mixtures listed in Table 1 were used. Composite 1 is based on monomer mixture 1, etc.
[2]Silanized alkaline glass with 47.4 wt.-% $SiO_2$, 39.8 wt.-% CaO, 8.4 wt.-% $Na_2O$, 7.6 wt.-% F.
[3]Silanized glass ionomer-fluorine-calcium-aluminium-silicate glass, average grain size 1.6 μm.
[4]Ytterbium fluoride (Rhône-Poulenc)
[5]Silanized pyrolysis silica (Degussa) primary particle size 40 nm, BET surface 50 $m^2/g$
[6]Silanized $SiO_2$-$ZrO_2$ mixed oxide (Tokoyama Soda), secondary particle size < 7 μm
[7]Highly-dispersed precipitation silica (Wacker)
[8]Silanized barium aluminum silicate glass powder (Schott), proportion with a grain size of < 7 μm: 99%

Testpieces were formed from the composite pastes in accordance with ISO standard 4049 (1988), cured by irradiation with light of a wavelength of 400–500 nm (2×3 minutes) and their mechanical properties were then determined.

To establish the fluoride-release capacity, cured testpieces (diameter=20 mm, H=1.5 mm) were stored in 30 ml of buffer solution at 37° C. in the agitator and the amount of released fluoride was measured after specific intervals using a fluorelectrode.

The results summarized in Table 3 show that the hydrophilic composite 1, which contains no acid or ionic monomer components, releases about ten times more fluoride ions within 28 days than does Compoglass®, a compomer customary in the trade that is based on COOH-acid monomers (filler: SP-2034 and YbF$_3$). The fluoride-ion release of composite 1 is thus of the same order as that of glass ionomer cements (cf. e.g. Vivaglass®, glass ionomer cement based on polyacrylic acid, filler: SP-2034 and YbF$_3$).

However, composite 1 displays clearly better mechanical properties and a higher resistance to water than do the compomer and the glass ionomer cement. Even six days' storage in water followed by 24-hour boiling scarcely impair the mechanical properties.

Uncured composite 1 was storage-stable under moist conditions (90% atmospheric humidity) over the 8-week investigation period.

If the hydrophilic GDMA in composite 1 is replaced by the hydrophobic TEGDMA (composite 2), a clearly smaller fluoride release is measured, although composite 2 contained, instead of SP-2034, a greater proportion of alkaline glass which displays a clearly higher fluoride release than SP-2034.

Composite 3 contains exclusively SP-2034 as ion-releasing filler. Its fluoride release is comparable with that of Compoglass® but, unlike Compoglass®, composite 3 is storage-stable in the uncured state even under moist conditions.

In composite 4, GDMA was replaced by TEGDMA. As in the case of composites 1 and 2, this replacement brings about a clear reduction in fluoride release.

In composite 5, the hydrophilic but multifunctional HEMA was used instead of GDMA. Although composite 5 displays a clearly higher fluoride release than does composite 4, the mechanical properties are unsatisfactory after the addition of water.

14-dioxa-5,12-diazahexa-decan-1,16-diyl-dimethacrylate (UDMA), a reaction product of glycidyl methacrylate with a bisphenol and/or a reaction product of 2 moles of 2-hydroxyethyl methacrylate (HEMA) or 2 moles of 2-hydroxypropyl(meth)acrylate with 1 mole of diisocyanate.

TABLE 3

Mechanical properties of cured composites

| Property | Composite 1 | Composite 2 | Composite 3 | Composite 4 | Composite 5 | Compoglass[1] | Vivaglass[2] |
|---|---|---|---|---|---|---|---|
| Bending strength[3] | | | | | | | |
| 24 h | — | — | 85 MPa | 112 MPa | 111 MPa | — | — |
| 24 h $H_2O$ storage | 122 MPa | 136 MPa | 92 MPa | 100 MPa | 100 MPa | 91 MPa | 28.0 MPa |
| 6 d $H_2O$ storage + 24 h boiling | 117 MPa | 105 MPa | — | — | — | 73 MPa | — |
| 7 d $H_2O$ storage | — | — | 75 MPa | 103 MPa | 77 MPa | — | — |
| Bending E-modulus[3] | | | | | | | |
| 24 h | — | — | 11.3 GPa | 9.7 GPa | 10.6 GPa | — | — |
| 24 h $H_2O$ storage | 11.4 GPa | 11.1 GPa | 11.5 GPa | 9.3 GPa | 9.5 GPa | 8.6 GPa | 2.0 GPa |
| 6 d $H_2O$ storage + 24 h boiling | 11.3 GPa | 8.2 GPa | — | — | — | 10.1 GPa | — |
| 7 d $H_2O$ storage | — | — | 9.7 GPa | 9.7 GPa | 7.8 GPa | — | — |
| F release[4] | 218[5] | 124[5] | 18.9[6] | 3.1[6] | 12.2[6] | 22[6] | 240[6] |

[1] Compomer on acid monomer basis, filler SP-2034, silanized (Vivadent)
[2] Glass ionomer cement on the basis of polyacrylic acid, filler SP-2034 (Vivadent)
[3] Determined in accordance with ISO standard 4049(1988) after the times given in the table
[4] Cumulative fluoride release after 25 days, given in $\mu g/cm^2$
[5] Measured in lactate buffer, 37° C.
[6] Measured in tris buffer, 37° C.

What is claimed is:

1. An ion-releasing composite material on the basis of polymerizable monomers, comprising a mixture of
   (a) 1 to 40 wt % of at least one non-acid, non-ionic, unsaturated, hydrophilic crosslinker monomer capable of hydrophilic interaction with a filler,
   (b) 2 to 40 wt % of at least one non-acid, non-ionic, hydrophilic dilution monomer having a viscosity of $\leq 1$ Pas and
   (c) 30 to 94 wt % of at least one ion-releasing filler, wherein the composite material has improved ion releasing capacity as compared to a composite material formulated with a hydrophobic dilution monomer.

2. A composite material according to claim 1, wherein the composite material further comprises:
   (d) 0.01 to 5 wt.-% of a radical initiator.

3. A composite material according to claim 2, wherein the composite material comprises:
   (a) 10 to 30 wt.-% of one or more crosslinker monomers;
   (b) 2 to 30 wt.-% of one or more dilution monomers; and/or
   (c) 0.1 to 2.0 wt.-% initiator.

4. A composite material according to claim 3, wherein the composite material comprises:
   (a) 15 to 25 wt.-% of one or more crosslinker monomers; and/or
   (b) 5 to 20 wt.-% of one or more dilution monomers.

5. A composite material according to claim 1, wherein the composite material further comprises 30 to 60 wt.-% (cement) or 60 to 64 wt.-% (filling composite) filler.

6. A composite material according to claim 1, wherein the crosslinker and/or dilution monomer or monomers contain urethane and/or OH groups.

7. A composite material according to claim 6, wherein the composite material comprises as the crosslinker monomer 2,2-bis-4-(3-methacryloxy-2-hydroxypropyl)-phenylpropane)(bis-GMA), 7,7,9-trimethyl-4,13-dioxo-3, 8. A composite material according to claim 1, wherein the composite material comprises as the dilution monomer glycerol dimethacrylate (GDMA), a reaction product of low-viscosity di- and triepoxides with (meth)acrylic acid and/or a reaction product of 2 or 3 moles of methacrylic acid with glycerol triglycidyl ether or trimethylol-propane triglycidyl ether.

9. A composite material according to claim 1, wherein the crosslinker and/or dilution monomer contains methacryl and/or acryl groups as groups capable of polymerization.

10. A composite material according to claim 1, wherein the composite material comprises as the initiator azobis-(isobutyronitrile), azobis(4-cyanovaleric acid), dibenzoyl peroxide, dilauroyl peroxide, tert.-butyl peroctoate, tert.-butyl perbenzoate, di-(tert.-butyl)-peroxide, benzpinacol, a 2,2'-di($C_1$–$C_8$-alkyl)benzpinacol, a benzoin ether, a dialkyl benzil ketal, dialkoxyaceto-phenone, acylphosphinic oxide, 9,10-phenanthrenequinone, diacetyl, fuiril, anisil, 4,4'-dichlorobenzil, 4,4'-dialkoxybenzil and/or camphor quinone.

11. A composite material according to claim 1, wherein the composite material comprises as the ion-releasing filler a filler releasing $Ca^{2+}$, $F^-$ and/or $OH^-$ ions.

12. A composite material according to claim 11, wherein the composite material comprises as the filler a glass powder of a fluoro-aluminium silicate glass having an average particle size of 0.05 to 15 $\mu$m.

13. A composite material according to claim 1, wherein the composite material further comprises an alkaline filler.

14. A composite material according to claim 13, wherein the composite material comprises as the filler calcium hydroxide, calcium oxide and/or a calcium hydroxide-releading glass powder.

15. A composite material according to claim 14, wherein the composite material comprises a glass powder having a CaO content of at least 20 wt.-%.

16. A composite material according to claim 15, wherein the glass powder contains 24.0 to 56.0 wt.-% $SiO_2$, 26.0 to 57.0 wt.-% CaO and 4.0 to 14.0 wt.-% F.

* * * * *